United States Patent [19]

Schwartz et al.

[11] Patent Number: 5,345,031
[45] Date of Patent: Sep. 6, 1994

[54] REDUCTION OF AROMATIC HALIDE CONTENT

[75] Inventors: Jeffrey Schwartz; Yumin Liu, both of Princeton, N.J.

[73] Assignee: The Trustees of Princeton University, Princeton, N.J.

[21] Appl. No.: 136,660

[22] Filed: Oct. 14, 1993

Related U.S. Application Data

[63] Continuation-in-part of Ser. No. 869,743, Apr. 16, 1992, abandoned.

[51] Int. Cl.$^5$ .............................................. C07C 1/26
[52] U.S. Cl. .................................. 588/206; 588/207; 588/248
[58] Field of Search .................. 588/206, 207, 248; 208/262.5, 262.1; 423/DIG. 20; 210/909

[56] References Cited

U.S. PATENT DOCUMENTS

| | | | |
|---|---|---|---|
| 4,188,346 | 2/1980 | Markley | 260/651 F |
| 4,447,667 | 5/1984 | Parker et al. | 585/469 |
| 5,004,551 | 4/1991 | Sublette | 210/763 |

OTHER PUBLICATIONS

Dennis, Jr. et al., *Bull. Environmental Contam. Toxicology*, vol. 22, pp. 750–753 (1979).
Meunier et al., *Journ. of Organometallic Chemistry*, vol. 204, pp. 345–346 (1981).

*Primary Examiner*—Michael Lewis
*Assistant Examiner*—Stephen G. Kalinchak
*Attorney, Agent, or Firm*—Mathews, Woodbridge & Collins

[57] ABSTRACT

The halide content of halogenated aromatic hydrocarbons such as PCBs can be reduced by treatment with a reagent comprising (i) at least one complex of a transition metal of group 4 or 5 with a multidentate or unidentate organic or inorganic ligand and (ii) a reducing agent. The reaction is conducted in the presence of an aliphatic or aromatic amine, optionally in the presence of an inert organic solvent.

10 Claims, No Drawings

REDUCTION OF AROMATIC HALIDE CONTENT

CROSS-REFERENCE TO RELATED APPLICATION

This is a continuation-in-part of Ser. No. 07/869,743 filed Apr. 16, 1992, now abandoned the disclosure of which is incorporated in its entirety herein by reference.

BACKGROUND OF THE INVENTION

In our copending Ser. No. 07/869,743, a process is described for the reduction of the chloride content of polychlorinated hydrocarbons such as, for example, polychlorinated benzene and polychlorinated biphenyls. The process utilizes a reagent comprising (i) at least one complex of a transition metal of group 4 or 5 with a multidentate or unidentate organic or inorganic ligand and (ii) a reducing agent such as a hydridoborate. Typical of the first component is bis-($\eta^5$-cyclopentadienyl)titanium dichloride (titanocene dichloride) while sodium tetrahydridoborate is representative of the latter.

The present process is based on the discovery that by conducting the reaction in the presence of an aliphatic or aromatic amine, the scope of the reaction can be expanded to other halogenated compounds and a greater degree of dehalogenation can be achieved.

The amine which is added can be any aliphatic amine such as trimethylamine, triethylamine, dimethylethylamine, etc., an aromatic amine such as N,N-dimethylaniline, N,N-dimethylnaphthylamine, etc., or an aromatic or nonaromatic heterocyclic amine such as pyridine, 1-methylimidazole, quinoline, piperidine, etc. Although primary and secondary amines can be employed, preferably the amine is a tertiary amine. Generally a molar excess of the amine is employed.

While other non-amine bases such as sodium methoxide appear to have a slight effect in accelerating the underlying reaction, this is by no means as dramatic as that observed upon addition of an amine.

The reaction can be conducted in a variety of inert organic solvents such as diglyme, triglyme, bis-(2-ethoxyethyl) ether, tetrahydrofuran, dimethylsulfoxide, dimethylformamide, ethylene glycol dimethyl ether and the like. Particularly preferred are ethers such as diglyme.

Optionally a phase-transfer agent can be added to assist in dissolution of the reactants, particularly the hydridoborate. Typical of these are the methyltri ($C_8$–$C_{10}$alkyl) ammonium chlorides.

The reaction can be conducted at temperatures of from about 50° C. to about 150° C. Selectivity in eliminating bromine atoms in the presence of chlorine atoms can be observed at the lower end of this range whereas at higher temperatures, i.e., at or above 100° C., complete removal of halogen atoms can be achieved even in polychlorinated compounds which are usually difficult to dechlorinate.

Reaction times will depend on the reactants and temperature. Operating at, for example, 125° C, complete dehalogenation can be observed in less than 10 hours. At lower temperature at which the reaction is more selective, the reaction times may increase 5 to 10 fold. In either case, the degree of dehalogenation can be readily monitored by conventional analytical techniques such as gas chromatography.

The following examples will serve to further typify the nature of the invention but should not be construed as a limitation on the scope thereof which is defined solely by the appended claims.

EXAMPLE 1

A reaction vessel is charged with 171 mg (0.687 mmol) of titanocene dichloride and 622 mg (16.4 mmol) of sodium tetrahydridoborate under a nitrogen atmosphere. A solution of 1000 mg of Aroclor 1248, a polychlorinated biphenyl (3.43 mmol, based on an average MW 292, assuming 13.7 mmol of C-Cl functional groups), and 1.35 ml of pyridine (16.7 mmol ) in 20 mL of bis-(2-methoxyethyl ) ether is added. The reaction mixture is heated at 125 ° C. One milliliter aliquots are withdrawn periodically, quenched with water, extracted with ethyl acetate, purified by passing through a short column of silica gel, and analyzed by gas chromatography. Significant dechlorination is observed after 3.5 hours with total dechlorination to biphenyl after 8.4 hours.

TABLE 1

| Peak | Chlorine Atoms | Retention Time (min) | Percent Start | Percent 3.5 Hrs | Percent 8.4 Hrs |
|---|---|---|---|---|---|
| 1 | 0* | 9.15 | 0.00 | 41.75 | 100.00 |
| 2 | 1 | 13.26 | 0.00 | 2.20 | 0.00 |
| 3 | 1 | 16.29 | 0.00 | 49.56 | 0.00 |
| 4 | 1 | 16.62 | 0.00 | 6.49 | 0.00 |
| 5 | 2 | 22.01 | 0.19 | 0.00 | 0.00 |
| 6 | 3 | 25.83 | 3.53 | 0.00 | 0.00 |
| 7 | 3 | 25.95 | 0.23 | 0.00 | 0.00 |
| 8 | 3 | 25.99 | 0.28 | 0.00 | 0.00 |
| 9 | 3 | 27.40 | 0.59 | 0.00 | 0.00 |
| 10 | 3 | 27.57 | 0.20 | 0.00 | 0.00 |
| 11 | 3 | 27.59 | 0.34 | 0.00 | 0.00 |
| 12 | 3 | 30.34 | 8.81 | 0.00 | 0.00 |
| 13 | 4 | 31.04 | 2.86 | 0.00 | 0.00 |
| 14 | 3 | 31.73 | 0.14 | 0.00 | 0.00 |
| 15 | 3 | 31.76 | 0.77 | 0.00 | 0.00 |
| 16 | 4 | 32.07 | 0.63 | 0.00 | 0.00 |
| 17 | 4 | 32.76 | 0.21 | 0.00 | 0.00 |
| 18 | 4 | 33.64 | 8.37 | 0.00 | 0.00 |
| 19 | 4 | 33.95 | 4.56 | 0.00 | 0.00 |
| 20 | 4 | 34.04 | 0.40 | 0.00 | 0.00 |
| 21 | 4 | 34.07 | 0.72 | 0.00 | 0.00 |
| 22 | 4 | 34.10 | 0.60 | 0.00 | 0.00 |
| 23 | 4 | 34.12 | 1.18 | 0.00 | 0.00 |
| 24 | 4 | 35.33 | 6.93 | 0.00 | 0.00 |
| 25 | 4 | 35.42 | 0.40 | 0.00 | 0.00 |
| 26 | 4 | 35.51 | 0.17 | 0.00 | 0.00 |
| 27 | 4 | 35.55 | 1.24 | 0.00 | 0.00 |
| 28 | 3 | 35.83 | 0.37 | 0.00 | 0.00 |
| 29 | 4 | 36.26 | 1.79 | 0.00 | 0.00 |
| 30 | 4 | 36.30 | 0.43 | 0.00 | 0.00 |
| 31 | 4 | 36.47 | 3.35 | 0.00 | 0.00 |
| 32 | 4 | 37.01 | 0.88 | 0.00 | 0.00 |
| 33 | 4 | 38.75 | 3.69 | 0.00 | 0.00 |
| 34 | 4 | 38.95 | 0.14 | 0.00 | 0.00 |
| 35 | 4 | 39.26 | 11.00 | 0.00 | 0.00 |
| 36 | 4 | 39.43 | 9.60 | 0.00 | 0.00 |
| 37 | 5 | 39.89 | 0.17 | 0.00 | 0.00 |
| 38 | 4 | 40.83 | 6.23 | 0.00 | 0.00 |
| 39 | 5 | 41.12 | 0.60 | 0.00 | 0.00 |
| 40 | 5 | 41.15 | 0.27 | 0.00 | 0.00 |
| 41 | 5 | 41.16 | 0.54 | 0.00 | 0.00 |
| 42 | 5 | 41.65 | 2.56 | 0.00 | 0.00 |
| 43 | 5 | 42.00 | 0.77 | 0.00 | 0.00 |
| 44 | 5 | 42.02 | 0.67 | 0.00 | 0.00 |
| 45 | 5 | 43.37 | 1.24 | 0.00 | 0.00 |
| 46 | 5 | 43.98 | 1.51 | 0.00 | 0.00 |
| 47 | 5 | 44.26 | 0.72 | 0.00 | 0.00 |
| 48 | 5 | 44.79 | 3.88 | 0.00 | 0.00 |
| 49 | 4 | 44.99 | 0.30 | 0.00 | 0.00 |
| 50 | 5 | 45.65 | 0.55 | 0.00 | 0.00 |
| 51 | 5 | 47.35 | 3.01 | 0.00 | 0.00 |
| 52 | 6 | 49.37 | 0.17 | 0.00 | 0.00 |
| 53 | 6 | 49.40 | 0.17 | 0.00 | 0.00 |
| 54 | 5 | 49.53 | 0.80 | 0.00 | 0.00 |
| 55 | 5 | 49.56 | 0.78 | 0.00 | 0.00 |

TABLE 1-continued

| Peak | Chlorine Atoms | Retention Time (min) | Percent Start | 3.5 Hrs | 8.4 Hrs |
| --- | --- | --- | --- | --- | --- |
| 56 | 5 | 49.59 | 0.44 | 0.00 | 0.00 |

\* = biphenyl

EXAMPLE 2

One hundred forth milligrams of titanocene dichloride (0.56 mmol), 378 mg of sodium tetrahydridoborate (10.0 mmol) and 190 mg of 4-bromochlorobenzene (1.0 mmol) are introduced into a reaction vessel under a nitrogen atmosphere and 10 mL of bis-(2-methoxyethyl) ether are added. The reaction mixture is heated at 50° C. and 1 mL aliquots are withdrawn periodically, quenched with water, extracted with diethyl ether, purified by passing through a short column of silica gel, and analyzed by gas chromatography.

TABLE 2A

| Time (hours) | (mole fraction) 4-Bromochlorobenzene | Chlorobenzene |
| --- | --- | --- |
| 0.00 | 1.00 | 0.00 |
| 9.17 | 1.00 | 0.00 |

After 9.2 hours, 41.2 mg of dimethylethylamine (0.56 mmol) are added and the reaction allowed to continue.

TABLE 2B

| Time (hours) | (mole fraction) 4-Bromochlorobenzene | Chlorobenzene |
| --- | --- | --- |
| 9.66 | 0.89 | 0.11 |
| 10.23 | 0.84 | 0.16 |
| 11.08 | 0.81 | 0.19 |

After 11.15 hours at 50° C., an additional 169 mg of dimethylethylamine (2.31 mmol) are added and the reaction allowed to continue.

TABLE 2C

| Time (hours) | (mole fraction) 4-Bromochlorobenzene | Chlorobenzene |
| --- | --- | --- |
| 13.40 | 0.70 | 0.30 |
| 13.75 | 0.47 | 0.53 |
| 14.28 | 0.23 | 0.77 |
| 14.97 | 0.09 | 0.91 |
| 15.85 | 0.00 | 1.00 |

EXAMPLE 3

One hundred twenty-five milligrams of titanocene dichloride (0.5 mmol), 454 mg of sodium tetrahydridoborate (12.0 mmol) and 1900 mg of 4-bromochlorobenzene (10.0 mmol) are introduced into a reaction vessel under a nitrogen atmosphere. Ten milliliters of bis-(2-methoxyethyl) ether and 1.65 mL of triethylamine (11.8 mmol) are added. The reaction mixture is heated at 73° C. and 1 mL aliquots are withdrawn periodically, quenched with water, extracted with diethyl ether, purified by passing through a short column of silica gel, and analyzed by gas chromatography. Reduction of 4-bromochlorobenzene is observed with a rate of $k_{obs} = 2.36 \times 10^{-2}$ $(h^{-1})$. The reaction is quenched after 93.6% conversion.

TABLE 3

| Time (hours) | (mole fraction) 4-Bromochlorobenzene | Chlorobenzene |
| --- | --- | --- |
| 0.00 | 1.00 | 0.00 |
| 17.70 | 0.761 | 0.239 |
| 40.67 | 0.393 | 0.607 |
| 53.30 | 0.301 | 0.699 |
| 68.28 | 0.227 | 0.773 |
| 89.32 | 0.123 | 0.877 |
| 168.17 | 0.064 | 0.936 |

EXAMPLE 4

One hundred twenty-five milligrams of titanocene dichloride (0.5 mmol), 378 mg of sodium tetrahydridoborate (10.0 mmol), 27 mg of sodium methoxide (0.5 mmol), and 190 mg of 4-bromochlorobenzene (1.0 mmol) are introduced into a reaction vessel under a nitrogen atmosphere and 10 mL of bis-(2-methoxyethyl) ether are added. The reaction mixture is heated at 50° C. and 1 mL aliquots are withdrawn periodically, quenched with water, extracted with diethyl ether, purified by passing through a short column of silica gel, and analyzed by gas chromatography.

TABLE 4A

| Time (hours) | (mole fraction) 4-Bromochlorobenzene | Chlorobenzene |
| --- | --- | --- |
| 0.067 | 0.977 | 0.023 |
| 0.442 | 0.976 | 0.024 |
| 1.083 | 0.965 | 0.035 |
| 3.567 | 0.837 | 0.163 |

After 3.75 hours, 416 mg of dimethylethylamine (5.69 mmol) are added and the reaction allowed to continue. The following results are obtained.

TABLE 4B

| Time (hours) | (mole fraction) 4-Bromochlorobenzene | Chlorobenzene |
| --- | --- | --- |
| 4.117 | 0.578 | 0.422 |
| 4.617 | 0.383 | 0.617 |
| 5.183 | 0.207 | 0.793 |
| 6.300 | 0.068 | 0.932 |
| 11.167 | 0.000 | 1.000 |

What is claimed is:

1. In the process of reducing halide content in halogenated aromatic hydrocarbons by reduction in the presence of a reagent comprising (i) at least one complex of a transition metal of group 4 or 5 with a multidentate or unidentate organic or inorganic ligand and (ii) a reducing agent, the improvement which comprises conducting the reduction in the presence of an aliphatic or aromatic amine and an inert organic solvent.

2. The process according to claim 1 wherein the halogenated aromatic hydrocarbons are polychlorinated aromatic hydrocarbons.

3. The process according to claim 2 wherein the polychlorinated aromatic hydrocarbons are polychlorinated biphenyls.

4. The process according to claim 1 wherein the amine is trimethylamine, triethylamine, dimethylethylamine, N,N-dimethylaniline, N,N-dimethylnaphthylamine, pyridine, 1-methylimidazole, quinoline, or piperidine.

5. The process according to claim 4 wherein the amine is triethylamine, dimethylethylamine, or pyridine.

6. The process according to claim 1 wherein the inert organic solvent is diglyme, triglyme, bis-(2-ethoxyethyl) ether, tetrahydrofuran, dimethylsulfoxide, dimethylformamide, or ethylene glycol dimethyl ether.

7. The process according to claim 6 wherein the inert organic solvent is diglyme.

8. The process according to claim 1 wherein the reduction is conducted at temperatures of from about 50° C. to about 150° C.

9. The process according to claim 1 wherein the complex is bis-($\eta^5$-cyclopentadienyl)titanium dichloride.

10. The process according to claim 1 wherein the reducing agent is sodium tetrahydridoborate.

* * * * *